US012566175B2

(12) United States Patent
Gajovic-Eichelmann et al.

(10) Patent No.: US 12,566,175 B2
(45) Date of Patent: Mar. 3, 2026

(54) METHOD FOR FUNCTIONALIZING A SURFACE, PRODUCT HAVING A SURFACE FUNCTIONALIZED ACCORDING TO SAID METHOD, AND USES THEREOF

(71) Applicant: Fraunhofer-Gesellschaft zur Förderung der angewandten Forschung e. V, Munich (DE)

(72) Inventors: Nenad Gajovic-Eichelmann, Berlin (DE); Marina Neumann, Potsdam (DE); Frank Bier, Potsdam (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 1034 days.

(21) Appl. No.: 17/434,104

(22) PCT Filed: Feb. 27, 2020

(86) PCT No.: PCT/EP2020/055101
§ 371 (c)(1),
(2) Date: Aug. 26, 2021

(87) PCT Pub. No.: WO2020/174032
PCT Pub. Date: Sep. 3, 2020

(65) Prior Publication Data
US 2022/0137044 A1 May 5, 2022

(30) Foreign Application Priority Data
Feb. 28, 2019 (DE) ..................... 10 2019 105 192.4

(51) Int. Cl.
*G01N 33/543* (2006.01)
(52) U.S. Cl.
CPC ................. *G01N 33/54393* (2013.01); *G01N 33/54366* (2013.01)

(58) Field of Classification Search
CPC ................... G01N 33/54393; G01N 33/54366
See application file for complete search history.

(56) References Cited

U.S. PATENT DOCUMENTS

| 3,057,792 A | 10/1962 | Fröhlich |
| 5,817,470 A | 10/1998 | Burzio et al. |
| | (Continued) | |

FOREIGN PATENT DOCUMENTS

| EP | 644904 | 3/1995 |
| GB | 190707775 | 7/1907 |
| | (Continued) | |

OTHER PUBLICATIONS

JP 2013067908 A, machine translation, originally published 2013, p. 1-17 (Year: 2013).*
Omura, K., "Oxidation of Phenols with Iodine in Alkaline Methanol", 1984, J. Org. Chem., 49, p. 3046-3050 (Year: 1984).*
(Continued)

*Primary Examiner* — Gordon Baldwin
*Assistant Examiner* — Christina D McClure
(74) *Attorney, Agent, or Firm* — Grüneberg Global IP, PLLC

(57) ABSTRACT

A method functionalizes a surface, wherein a polyphenol layer is formed on the surface by applying a polyphenol compound, and the surface is subsequently functionalized by binding a functional molecule to the polyphenol layer. In addition, the polyphenol layer is treated with an oxidizing agent before, during, or after binding of the functional molecule. An associated article can be prepared and used. A kit can be used for performing the method or producing the article.

19 Claims, 4 Drawing Sheets

(56) References Cited

U.S. PATENT DOCUMENTS

| 2010/0158885 A1* | 6/2010 | Huang | A61P 43/00 |
| | | | 568/717 |
| 2013/0203171 A1* | 8/2013 | Sportsman | G01N 33/146 |
| | | | 436/24 |
| 2013/0224795 A1* | 8/2013 | Park | A61L 33/0047 |
| | | | 435/129 |

FOREIGN PATENT DOCUMENTS

| GB | 260290 | 4/1928 |
| JP | 2013-67908 | 4/2013 |
| WO | 93/25594 | 12/1993 |
| WO | 2014/116812 | 7/2014 |

OTHER PUBLICATIONS

Gardner, W., et al., "CCII.—The Iodination of Phenols and the Iodometric Estimation of, and Action of Reducing Agents on, Tannic Acid", 1909, J. Chem. Soc., Trans., 95, p. 1819-1827 (Year: 1909).*

International Search Report issued May 25, 2020 in PCT/EP2020/055101 with English translation, 6 pages.

Kumar et al., "*Universal method for direct bioconjugation of electrode surfaces by fast enzymatic polymerization*", Biosensors and Bioelectronics, vol. 127, 2019, pp. 50-56.

Liao et al., "*Polyphenol-Reduced Graphene Oxide: Mechanism and Derivatization*", The Journal of Physical Chemistry, American Chemical Society, vol. 115, 2011, pp. 20740-20746.

Written Opinion issued May 25, 2020 in PCT/EP2020/055101 with English translation, 13 pages.

* cited by examiner

METHOD FOR FUNCTIONALIZING A SURFACE, PRODUCT HAVING A SURFACE FUNCTIONALIZED ACCORDING TO SAID METHOD, AND USES THEREOF

CROSS-REFERENCE TO RELATED APPLICATIONS

This patent application is the National Stage entry under $371 of International Application No. PCT/EP2020/055101, filed on Feb. 27, 2020, and which claims priority to German Patent Application No. 10 2019 105 192.4, filed on Feb. 28, 2019. The content of each of these applications is hereby incorporated by reference in its entirety.

BACKGROUND OF THE INVENTION

Field of Invention

The present invention is in the field of selective modification of surfaces of technical materials such as plastics, metals, semiconductors, ceramics and glasses with functional molecules such as proteins, nucleic acids, polyelectrolytes and functional polymers. Such surfaces are used in analytical and diagnostic tests as well as in medical devices, among other applications.

Description of Related Art

A large number of technical, biotechnological and medical applications require attaching natural, biological or synthetic molecules to surfaces of a wide variety of materials in order to impart them with specific properties. Important examples are the coupling of antibodies or antigens to the surface of disposable plastic articles such as microtiter plates in clinical diagnostics, the coupling of ion exchange polymers to the surface of membranes and filters made of natural or synthetic polymers for separation and purification processes, or the coating of medical implants with growth factors or antibiotics to improve healing or prevent implant-associated infections.

A key challenge is that many materials used in technology have an essentially inert or low-energy surface and, accordingly, there are hardly any or no chemical groups available on such substrates that are suitable for the physical or chemical binding of molecules embodying specific functions, so-called functional molecules.

In order to be able to attach functional molecules to such substrates, also referred to as "immobilization" in the following, the surfaces must typically first be converted into high-energy surfaces with the use of laborious processes.

Complicating matters further is the fact that functional molecules, especially those of biological origin, are usually very sensitive and can only be used under gentle conditions, for example in aqueous solution with a neutral pH and at temperatures below about 40° C. Under such reaction conditions, the physical or chemical binding of functional molecules usually proceeds slowly and can lead to incomplete or uneven surface coverage.

Various methods are known for increasing the surface energy. Metals and semiconductors, for example, can be coated with a high-energy oxide layer by chemical, plasma-chemical or electrochemical oxidation. This layer can then be chemically modified with, for example, silane or phosphoric acid derivatives to enable the bonding of functional molecules. In principle, ceramics and glasses can be functionalized in a similar way. The disadvantage is that these methods typically involve several process steps with very different technical requirements, such as plasma chemical oxidation and a series of different wet chemical treatments in organic and aqueous media. Such surfaces can therefore often only be produced with a high level of equipment and time expenditure.

The functionalization of plastics poses a particular challenge, as they have the comparatively lowest-energy surfaces among the commonly used technical materials. On the other hand, plastic articles are usually relatively inexpensive and are therefore often produced as disposable articles, e.g. for bioanalytics, diagnostics and medicine, in very high quantities, so that a suitable functionalization method should be quickly performable and as inexpensive as possible.

U.S. Pat. No. 3,057,792 A discloses a method in which oxygen or nitrogen groups are introduced by plasma treatment or corona discharge to increase the surface energy of plastics. In EP 0 644 904 A1, a method is disclosed in which plastic surfaces are coated with a thin layer of lacquer or a reactive polymer thin film to enable binding of biologically active molecules. A disadvantage of these methods is the relatively high technical effort and the often insufficient durability or stability of the resulting surfaces, so that correspondingly treated plastic articles are too expensive or impractical for many applications.

For this reason, the production of disposable products for laboratory diagnostics, for example, still predominantly relies on functionalization by direct adsorption of functional molecules such as proteins on plastic surfaces, which is technically much easier to implement. Surface adsorption or surface adhesion is hereby based on partial unfolding and denaturation of the proteins on the hydrophobic plastic surface. This method is not only lengthy and relatively inefficient, but also results in a large proportion of the surface-bound proteins being denatured and inactive. Due to the usually high-value proteins, this not only significantly increases the manufacturing costs, but can also make it difficult to reproduce the products manufactured in this way.

Finally, in WO 2014/116812 A2, the property of polyphenols to form hydrophilic layers on a wide variety of surfaces that has long been known from GB 190707775 A and GB 260290 A, among others, is used to first generate a polyphenol layer on a plastic, metal or ceramic surface, to which a polymer or a protein, for example, can subsequently be attached.

The methods known to date for the production of functionalized surfaces still have various disadvantages. In particular, low efficiency of one or more method steps, a low degree of functionalization and/or insufficient stability of the resulting surfaces can be limiting factors.

SUMMARY OF THE INVENTION

It is therefore a problem to be solved by the present invention to provide an improved method for the functionalization of surfaces or corresponding articles with improved properties with respect to one or more of the above-mentioned disadvantages. In particular, it is a problem to be solved by the present invention to provide an improved method for the functionalization of plastic surfaces with proteins, in particular with antibodies, for an application in analytics or diagnostics and correspondingly improved articles which can be manufactured with this method.

These problems are solved according to the invention as described below. Further embodiments as well as preferred and advantageous variants are also described below.

DETAILED DESCRIPTION OF THE INVENTION

Definitions and General Explanations

Figure 1:
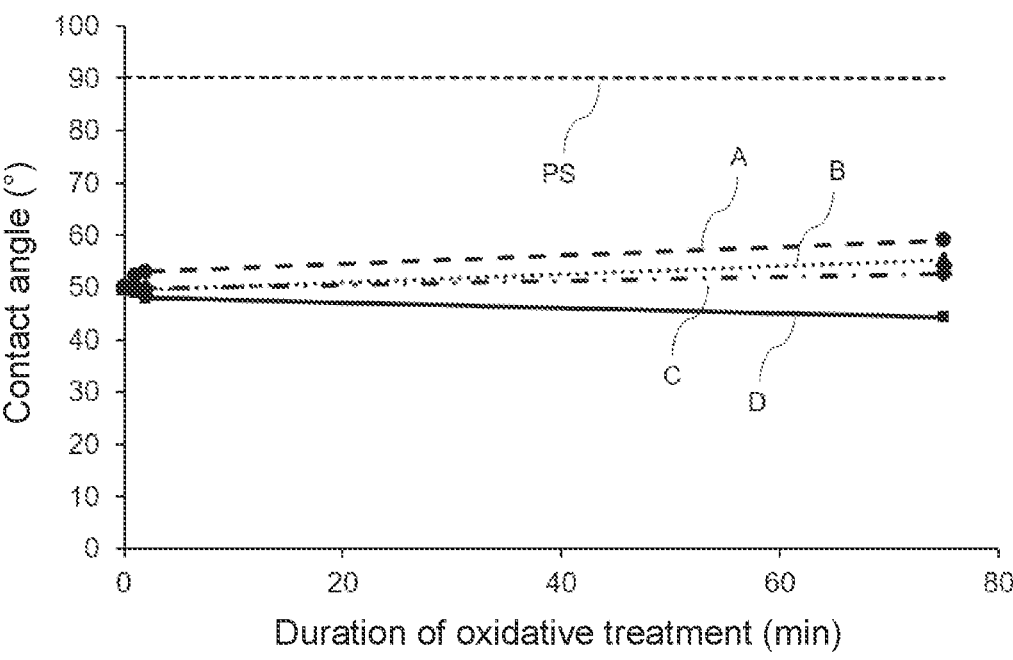
FIG. 1 shows a graph of the water contact angles in degrees of tannic acid layers on polystyrene as a function of the duration in minutes of an oxidative treatment with iodine or iodine starch of different composition.

Various documents are cited in this description to provide a general technical background relating to the present invention.

The disclosure and teachings of these documents are referred to in their entirety in addition to the following description in order to more fully describe the prior art upon which the present invention is based.

The following definitions and general explanations are intended to guide and assist the skilled reader in the understanding, interpretation and practice of the present invention. Unless otherwise indicated, all technical and scientific terms are intended to have the meaning which corresponds to the ordinary understanding of terms of an average person skilled in the art of the present invention.

As used here, indefinite articles such as "a" or "an" include the possibility that two or more of these features may also be present.

A "functional molecule" in the sense of the present invention can be any molecule that has a specific and/or technically useful physical, chemical and/or biological property or activity. In certain variants of the invention, a functional molecule is understood to be a biomolecule such as a protein, for example, an enzyme, an antigen or an antibody, or a nucleic acid. In yet other variants of the invention, a functional molecule may include a chemical molecule, in particular a polymer such as a polyelectrolyte or a functional polymer.

Accordingly, "functionalization" means imparting a specific physical, chemical or biological property to a surface, in particular a property that is not inherent to the surface itself, by means of attaching of such a functional molecule.

The "degree of functionalization" is understood to be the ratio of those functional molecules which are bound to the surface in active or functional form to those which have lost their function through surface binding.

As used herein, the term "attaching" or "attachment" can mean both the formation of a physical or adsorptive bond and the formation of a chemical or covalent bond to a surface, especially a solid surface.

"Polyphenol compounds" or "polyphenols" are used herein as a collective term for a diverse structural class of chemical compounds characterized by one or more structural units having two or more hydroxy groups (—OH) directly attached to one or more aromatic rings, hereinafter also referred to as "phenol group". Within a polyphenol compound, an aromatic ring with two hydroxy groups as substituents is hereinafter referred to as a "diphenol group", and with three hydroxy groups as substituents as a "triphenol group". Two vicinal hydroxy groups within a diphenol group or triphenol group are also referred to hereinafter as an "ortho-diphenol group". In addition to hydroxy groups, polyphenols may further contain other heteroatom substituents such as ether and ester groups and carbonyl and carboxyl groups. In preferred embodiments of the present invention, polyphenol compounds are nitrogen-free chemical compounds.

Accordingly, a "polyphenol layer" corresponds to a layer on a surface which comprises or consists of one polyphenol or one polyphenol compound or several polyphenols or polyphenol compounds. As the term is used herein, "polyphenol layer" expressly also includes those layers which have been treated with an oxidizing agent in accordance with the present invention or in which at least some of the polyphenol compounds present in the layer have been converted into an oxidized form or have been present in an oxidized form for at least some time.

An "oxidizing agent" is a substance that can oxidize other substances in a redox reaction and is itself reduced in the process. Oxidizing agents can accept electrons and are therefore also called electron acceptors.

The term "quinone" is used herein to describe an oxidation product of a polyphenol or polyphenol compound in which the hydroxyl groups of a diphenol group or triphenol group are replaced by double-bonded oxygen on two carbon atoms, thereby eliminating the aromaticity of the ring. A distinction is made between a 1,2-(ortho)quinone, hereinafter also referred to as "ortho-quinone group", and a 1,4-(para)quinone, hereinafter also referred to as "para-quinone group".

Both the foregoing general description and the following detailed description are to be understood as examples and are intended to explain the present invention. Further advantages and features of the invention are apparent from the description below and the drawings.

DESCRIPTION OF THE INVENTION

According to a first aspect of the invention, a method for functionalizing a surface is provided. In this method, a polyphenol layer is first generated on at least a part of the surface by applying or depositing at least one polyphenol compound. In a subsequent method step, at least one functional molecule is then attached to the polyphenol layer, thereby functionalizing the surface. In this context, the method according to the present invention is characterized in that, in a further step, the polyphenol layer is treated at least partially with an oxidizing agent. Herein, the treatment with the oxidizing agent can be carried out before and/or after the attachment of the functional molecule, but treatment during the attachment of the functional molecule is also possible. In a preferred method variant, the treatment of the polyphenol layer with the oxidizing agent is carried out at least partially, preferably completely, after the functional molecule has been attached to the polyphenol layer. In the latter case, the attachment of the functional molecule and the subsequent treatment with the oxidizing agent are therefore separate method steps.

The inventors have recognized that surface functionalization using polyphenol layers according to the teachings of WO 2014/116812 A2, despite having principal advantages, is often not sufficient alone to meet the high requirements in terms of degree of functionalization, stability, reproducibility and cost efficiency that are demanded of the functionalized surfaces of analytical and diagnostic products, for example. While it is desirable for most (bio)technical and medical applications of immobilized proteins, such as immunoassays, cell culture plates, medical devices and implants, to immobilize the proteins as irreversibly as possible while largely preserving their functionality, the inventors were able to find out in extensive investigations that proteins bind predominantly reversibly, i.e. with low binding energy, to polyphenol layers. Due to the low binding energy, the proteins can spontaneously detach from the surface again or be displaced from it by other proteins or substances with higher surface affinity. This is particularly problematic in analytical and diagnostic applications, as these effects can lead to strong variations in results and significantly impair quality characteristics such as the reproducibility and precision of such applications.

The present invention solves this problem by additionally treating the polyphenol layer with an oxidizing agent for improved binding of functional molecules. By means of this oxidation step, the polyphenol compound in the layer is at least partially converted into an oxidized or reactive form and thereby enabled to form a covalent bond to the functional molecule. Compared to adsorption, the covalent bond leads to an improved stability of the attachment product and the functional molecules can be immobilized in a higher density on the surface. In particular, oxidation of the polyphenol compound can form a reactive quinone to which the functional molecule can be nucleophilically attached, e.g. via amino, thiol and/or hydroxyl groups. In this way, functional molecules, in particular proteins, which are only bound to the polyphenol layer by adsorption, and thus reversibly, by previously known methods, are covalently and thus essentially irreversibly coupled to the surface with the aid of the oxidation treatment, without the need to add further chemical activation reagents to the reaction as in conventional bioconjugation techniques.

The combined effect of the advantageous property of polyphenol compounds of forming highly energetic, readily water-wettable layers on low-energy substrates of various types and the advantages of a largely irreversible binding of functional molecules to the polyphenol layers with the aid of the additional oxidation treatment of the layers provides a more universal, time- and cost-efficient solution for the functionalization of surfaces for a wide variety of applications than the methods known in the prior art. In this respect, reference is also made to the following description and the examples.

Basically, any polyphenol compound known to the skilled person as suitable for this purpose from the prior art, for example WO 2014/116812 A2, can be used to produce the polyphenol layer. In particular, it can be a naturally occurring or plant polyphenol compound. These are generally readily available, inexpensive and non-toxic, which on the one hand simplifies the handling of the compounds and the performance of the method, and on the other hand is an important characteristic if the functionalized surfaces are intended for use on or in the human body, as is the case, for example, with medical implants.

It is also advantageous if the polyphenol compound is substantially free of amines ($-NR_3$) or amino groups ($-NH_2$) or contains no amines or amino groups. The inventors have recognized that the use of amine-containing polyphenol compounds in the method of the invention can result in colored, dark polyphenol layers. With amine-free polyphenol compounds, on the other hand, transparent and colorless polyphenol layers can be produced by the method according to the present invention, which are preferred in particular for many applications in analysis and diagnostics.

In preferred embodiments of the method, the polyphenol compound has at least one ortho-diphenol group, which is converted into an ortho-quinone group by treatment with the oxidizing agent. The inventors have found that a particularly high reactivity of the oxidized polyphenol layer can be achieved in this way, which ensures a particularly fast and efficient covalent binding of the functional molecule even under mild or physiological reaction conditions. Such fast and efficient binding reactions not only reduce the process time considerably, but are also of particular benefit for largely preserving the function of sensitive functional molecules, such as proteins. Due to combination of these advantages, efficient functionalization or a high degree of functionalization of the modified surface can be achieved with the method according to the present invention, even with the use of small amounts of the functional molecule.

The polyphenol compound may comprise, or consist of, a tannin, in particular a gallotannin or an ellagitannin, or a catechin, for example. Preferably, the polyphenol compound is selected from the group comprising or consisting of tannic acid, gallocatechin, epicatechin, epigallocatechin, epicatechin gallate, epigallocatechin-3-gallate, and pyrogallol. Naturally, two or more different polyphenol compounds can also be used to generate the polyphenol layer, so that any combination of the aforementioned compounds is also possible. It is particularly preferred that the polyphenol compound comprises tannic acid.

In principle, the polyphenol compound can be applied using any of the methods described in the prior art for producing a polyphenol layer. Suitable methods are known to the skilled person from WO 2014/116812 A2, GB 190707775 A and GB 260290 A, for example.

In preferred embodiments of the method, the polyphenol compound is contained in a coating solution, preferably aqueous, with which the surface is contacted under conditions that result in deposition of the polyphenol compound on the surface to produce the polyphenol layer. The polyphenol compound may be present, for example, in a concentration of 0.1 to 10 milligrams per milliliter, preferably 0.5 to 5 milligrams per milliliter, more preferably 1 to 2 milligrams per milliliter in the coating solution.

Surprisingly, it is advantageous for the functionalization of surfaces according to the present invention if the deposition of the polyphenol compound is carried out under milder conditions and/or for a shorter time than is the case with previously known methods.

In a preferred embodiment, the pH of the coating solution is greater than or equal to pH 6.0, greater than or equal to pH 6.5 or greater than or equal to pH 7.0 and/or less than or equal to pH 9.0, less than or equal to pH 8.0 or less than or equal to pH 7.5. Preferably, the pH of the coating solution is in a range from pH 7.0 to pH 7.6, in particular pH 7.2 to pH 7.5. To buffer the pH, the coating solution can usefully contain one or more buffer substances. Suitable buffers, such as phosphate buffers, are known to those skilled in the art or can be readily determined on the basis of this description. Inorganic or amine-free buffer substances are preferred.

In another embodiment, the coating solution contains a salt or a mixture of salts in a concentration of at least 50 millimoles per liter, at least 100 millimoles per liter or at least 150 millimoles per liter and/or not more than 500 millimoles per liter, not more than 300 millimoles per liter or not more than 200 millimoles per liter. Preferably, the concentration is in the range of 50 to 500 millimoles per liter, more preferably 100 to 250 millimoles per liter, most preferably 120 to 200 millimoles per liter. Physiological salt concentrations around 150 millimoles per liter have been found to be particularly advantageous for the method according to the invention. The salt or mixture of salts may comprise, for example, a sodium salt, a potassium salt, a calcium salt, a magnesium salt, a copper salt, a zinc salt, or any combination thereof. In particular, the salt or mixture of salts may be selected from NaCl, NaNO$_3$, Na$_2$SO$_4$, KCl, K$_2$SO$_4$, MgCl$_2$, CaCl$_2$, CuCl$_2$, and/or ZnCl$_2$.

According to another preferred embodiment, the surface is contacted with the coating solution for at least 1 minute, at least 10 minutes, at least 20 minutes or at least 30 minutes and/or not more than 120 minutes, not more than 90 minutes or not more than 60 minutes. For example, the contact time may be from 1 to 120 minutes, preferably from 10 to 90 minutes, more preferably from 30 to 70 minutes, most preferred from 40 to 60 minutes. It is a particular advantage of the method according to the present invention that polyphenol layers particularly suitable for functionalization can be produced in a shorter time than suggested by previously known methods. As a result, the method according to the present invention provides improved efficiency compared to conventional methods and enables a higher production throughput, which is particularly suitable for mass production. In addition, the coating solution has a low viscosity, so that, for example, the surfaces of porous materials such as filters, membranes and open-pored foams can also be coated by the use of simple means. For example, the coating solution can have a viscosity of from 1 to 100 millipascal seconds, preferably from 2 to 20 millipascal seconds, particularly preferred from 2 to 10 millipascal seconds.

For the oxidation step, the polyphenol layer can in principle be contacted with any suitable oxidizing agent and under conditions that result in the polyphenol compound in the layer being at least partially converted into an oxidized form. In addition to a preferred chemical oxidation, enzymatic oxidation is also possible, for example.

Preferred oxidizing agents are, for example, hydrogen peroxide (H$_2$O$_2$), elemental iodine (I$_2$) and/or iodide, wherein the oxidizing agent can be present in particular in the form of a buffered, aqueous oxidant solution or is contained therein. Suitable concentrations of the aforementioned oxidizing agents in the oxidant solution are, for example, in the range of 0.01 to 100 milligrams per milliliter of iodine and/or iodide or 0.01 to 10% (v/v) hydrogen peroxide. The inventors have found that with these oxidizing agents, e.g. with elemental iodine (I$_2$), the polyphenol layer can be oxidized within a very short time without adversely affecting the properties or quality of the polyphenol layer, such as transparency and hydrophilicity, due to undesirable side reactions.

In preferred embodiments, the polyphenol layer is treated with the oxidizing agent for at least 10 seconds, at least 30 seconds, or at least 60 seconds and/or not more than 75 minutes, not more than 60 minutes, not more than 45 minutes, not more than 30 minutes, not more than 15 minutes, not more than 10 minutes, or not more than 5 minutes. Preferred treatment times range from 0.1 to 75 minutes, 0.5 to 30 minutes, or 1 to 5 minutes. In this way, the polyphenol layer can be oxidized very efficiently and without damage or undesirable side reactions.

Surprisingly, it has been found to be particularly advantageous if the iodine and/or iodide is present at least partially as an iodine-iodide-starch complex or polyiodide-starch complex, hereinafter also referred to as iodine starch. Such complexes are obtainable, for example, by mixing elemental iodine or iodine-iodide solutions (e.g. iodine-potassium iodide solution or iodine-sodium iodide solution) with starch, in particular water-soluble starch. Suitable oxidant solutions may contain about 0.01 to 80 milligrams per milliliter or about 10 to 50 milligrams per milliliter of starch, about 0.01 to 100 milligrams per milliliter or about 0.1 to 10 milligrams per milliliter of iodine and/or about 0.01 to 100 milligrams per milliliter or about 0.1 to 10 milligrams per milliliter of iodide, in particular sodium and/or potassium iodide. In the context of the present invention, it was recognized for the first time that when iodine starch is used, the oxidizing effect of elemental iodine can be utilized, but at the same time the reactivity of the iodine is reduced to such an extent that the reaction time and effective dose can be better controlled than when pure iodine is used.

Without being bound by theory, it is assumed that the iodine or iodide is chemically stably bound by inclusion in the helical starch molecules and is little or no reactive at all. Only upon contact or reaction with the polyphenol layer does the inclusion compound begin to break down, e.g. by cross-linking the starch, causing the iodine or iodide to be released locally and oxidize the polyphenol compound. Reactive iodine or iodide is therefore not released in the volume, but directly at the interface with the polyphenol layer, and only as long as oxidizable phenol groups are still present in the polyphenol layer. This hitherto completely unknown form of self-regulating oxidation effect of iodine starch makes it possible with the method according to the present invention, for example, to avoid oxidative damage to the functional molecules if the polyphenol layer is treated with the oxidizing agent already during the attachment of the functional molecule or after the attachment of the functional molecule, as provided in preferred method variants.

In addition, iodine starch has a concentration-dependent blue, blue-violet to black coloration and decolorizes with the decomposition of the inclusion compound. This has the advantage that in the method according to the invention the course of the reaction during the oxidative treatment of the polyphenol layer can be easily followed optically or the end point of the reaction can be easily determined, e.g. with the naked eye or by means of optical measuring methods such as photometry or colorimetry. This makes the method more time-efficient and further improves the reproducibility of manufactured articles.

As a further benefit, the inventors have found that the starch can also react with the oxidized polyphenol layer during the oxidation step itself, e.g. by nucleophilic addition. On the one hand, this causes irregular crosslinking of the polyphenol compounds within the layer by the long-chain starch molecules, resulting in a significant improvement in the stability of the polyphenol layer. On the other hand, the starch attachment additionally increases the hydrophilicity of the surface and makes it chemically inert. This is particularly advantageous in microfluidic, analytical, and diagnostic applications, as in this way undesired reactions of the surface, such as non-specific protein binding, can be significantly reduced compared to conventional polyphenol surfaces. Therefore, the method according to the present invention is particularly suitable for the preparation of solid-phase reagents for bioanalytical or immunological tests such as ELISA (enzyme-linked immunosorbent assay) as well as for the hydrophilization or passivation of microfluidic devices and systems, in particular so-called lab-on-chip devices. In certain method variants, starch itself can therefore also be used as a functional molecule in the sense of the present invention, e.g. if the functionalization is primarily aimed at hydrophilization or passivation of the surface.

The attachment of the functional molecule to the polyphenol layer is preferably carried out from a solution, hereinafter also referred to as functionalization solution, with which the polyphenol layer is contacted under conditions that allow the functional molecule to bind or adsorb to the surface of the polyphenol layer. For functional molecules of biological origin, such as proteins, aqueous, salt-containing buffer solutions with essentially physiological ionic strength and a pH in the range from pH 5.0 to pH 9.0 are particularly suitable as functionalization solutions. For example, a physiological phosphate-buffered salt solution (PBS buffer) with pH 7.4 is suitable. Other suitable buffer solutions are known to the person skilled in the art or can be readily determined on basis of the present description.

In preferred embodiments, the functionalizing solution contains at least 0.01 microgram per milliliter, at least 0.05 microgram per milliliter or at least 0.1 microgram per milliliter and/or not more than 10 milligrams per milliliter, not more than 1 milligram per milliliter, not more than 100 micrograms per milliliter, not more than 10 micrograms per milliliter, not more than 3 micrograms per milliliter or not more than 1 microgram per milliliter of the functional molecule. Preferably, the concentration of the functional molecule is in a range from 0.01 microgram to 10 milligrams per milliliter, in the case of proteins or antibodies in particular in a range of 0.01 to 100 micrograms per milliliter, preferably 0.02 to 50 micrograms per milliliter, more preferably 0.05 to 10 micrograms per milliliter, particularly preferred 0.1 to 3 micrograms per milliliter or 0.1 to 1 micrograms per milliliter, in particular 0.2 to 0.8 micrograms per milliliter. Remarkably, it has been shown that significantly lower amounts and higher dilutions of the functional molecule can be used for surface functionalization according to the invention compared to conventional methods in order to achieve the same or even better functionalization results. In this regard, reference is also made to the following examples. As a result, it is regularly possible to save 50% or more of the functional molecule, which is usually the most expensive component of functionalization processes.

It is of course also possible to attach more than one functional molecule to the surface. The functional molecule can, for example, be contained in a mixture of at least two or more different functional molecules, in which case the total concentration of the functional molecules in the mixture preferably corresponds to the aforementioned concentration specifications. It is a particular advantage of the process according to the invention that different functional molecules with different physicochemical properties can also be presented side by side on the functionalized surface due to the formation of an essentially irreversible, covalent bond to the oxidized polyphenol layer while at the same time maintaining a high speed of the binding reaction. So far, this has hardly been possible in a reproducible way with conventional adsorption-based methods, because in this case the reaction rate and binding energy depend on the individual physicochemical properties of the different functional molecules. Since adsorption usually favors the binding of molecules with high abundance and/or high surface affinity and, moreover, during the establishment of a stable absorption equilibrium in the presence of several proteins, a displacement of low-affinity molecules by high-affinity molecules can occur, a reproducible or controllable surface functionalization by adsorptive coupling of mixtures of different functional molecules is hardly or not at all feasible.

In preferred embodiments, the polyphenol layer is contacted with the functional molecule or with the functionalization solution for at least 1 minute, at least 2 minutes, at least 3 minutes or at least 5 minutes and/or for not more than 120 minutes, not more than 60 minutes or not more than 30 minutes. Preferred contact times are in the range of 1 to 120 minutes, preferably 2 to 60 minutes, particularly preferred 5 to 30 minutes.

Preferably, the binding of the functional molecule is carried out at a temperature of 10° C. to 60° C., preferably 15° C. to 40° C., more preferably 20° C. to 37° C. or 20° C. to 25° C. To improve mass transfer, it is also possible to carry out mixing, for example by stirring or shaking, at least intermittently during the attachment reaction. Within the aforementioned parameters, the method according to the invention achieves a particularly homogeneous and high-grade functionalization of the surface.

In principle, the method according to the present invention is suitable for all functional molecules that can react with the oxidized form of the polyphenol layer and, in particular, can form a covalent bond. Accordingly, non-limiting examples are chemical or biological functional molecules which contain at least one nucleophilic group such as an amino group ($-NH_2$), a thiol group ($-SH$) and/or a hydroxy group ($-OH$). With particular preference, the functional molecule is a biomolecule, for example a protein and, in particular, an antibody, which can be coupled to the surface particularly gently under the above-mentioned conditions and, in contrast to conventional methods, securely while largely retaining the biological or biochemical function.

The inventors have also found that, in practical use, the polyphenol layer of surfaces functionalized in conventional manner can tend to non-specifically adsorb e.g. proteins and other surface-affine molecules. This is a particular problem in analytical and diagnostic applications such as immunoassays, biosensors, and similar systems, since high nonspecific binding of proteins from, for example, blood plasma, serum, and other body fluids can severely impair the quality and reliability of such test systems. To make matters worse, according to the findings of the inventors conventional polyphenol coatings often lack the temperature stability and long-term stability required for a variety of products such as diagnostics and medical devices. These disadvantages have not yet been recognized in the prior art, let alone solved in a satisfactory technical manner.

Surprisingly, both problems can be solved by additionally treating the polyphenol layer at least partially with at least one di- or multivalent nucleophile, i.e. a compound with two or more nucleophilic groups, hereinafter also referred to as blocking or crosslinking step. The blocking or cross-linking step may be carried out after the functional molecule is attached, after treatment with the oxidizing agent and/or during treatment with the oxidizing agent. In preferred embodiments, the blocking or crosslinking step is carried out after the functional molecule is attached and after treatment with the oxidizing agent. Preferably, the functional molecule and the di- or multivalent nucleophile are different molecules. However, it is also possible that the blocking or crosslinking step involves or replaces the attachment of the functional molecule in that the di- or multivalent nucleophile is also a functional molecule, for example a protein that contributes to the inertization and/or hydrophilization of the surface. Without being bound by theory, it is assumed that di- or multivalent nucleophiles react covalently with the oxidized polyphenol layer, causing on the one hand a stabilizing cross-linking and on the other hand a surface saturation of the polyphenol layer, which significantly reduces the adsorption influence of the surface. These effects are also evident from the following examples.

In particular, the nucleophilic groups comprise two or more groups selected from —NH$_2$, —SH, —OH, and any combinations thereof. Suitable nucleophiles may include proteins, protein fragments, peptides, polyethylenimine, poly-L-lysine, polyvinyl alcohol, hydroxyethylcellulose, pectin, starch, and any combinations thereof. Some non-limiting examples include bovine serum albumin (BSA), casein, gelatin, or fragments thereof. Preference is given to a mixture of protein fragments derived from gelatin, which is highly soluble in water at room temperature and forms low viscosity solutions.

In preferred embodiments, the polyphenol layer is treated with the di- or multivalent nucleophile for at least 10 minutes, preferably at least 20 minutes, more preferably at least 30 minutes and/or not more than 600 minutes, preferably not more than 240 minutes, more preferably not more than 120 minutes. Preferably, the treatment time is 10 to 600 minutes, in particular 30 to 240 minutes.

Preferably, the treatment with the di- or multivalent nucleophile is carried out by contacting the polyphenol layer with a solution containing at least 0.1 weight percent, preferably at least 0.5 weight percent, more preferably at least 1 weight percent and/or not more than 50 weight percent, preferably not more than 10 weight percent, more preferably not more than 2 weight percent of the di- or multivalent nucleophile. Suitable concentrations range from 0.1 to 50 weight percent, 1 to 10 weight percent and 0.5 to 2 weight percent.

As has been repeatedly pointed out above, the sequence of the methods steps according to the invention is not particularly limited. Although the attachment of the functional molecule to the polyphenol layer is preferably carried out before the treatment of the polyphenol layer with the oxidizing agent, it is also possible to oxidize the polyphenol layer first and then attach the functional molecule to it. Another possibility is to combine the attachment of the functional molecule and the treatment with the oxidizing agent at least partially or completely in one step. This can be particularly useful if denaturation of the functional molecule by the oxidizing agent is not to be expected. Furthermore, it has been shown that an oxidation treatment during the attachment of the functional molecule can lead to a beneficial acceleration of the binding reaction. In further variants, the two treatments with the oxidizing agent and with the di- or multivalent nucleophile can be switched or combined into one step, i.e., oxidation and simultaneous blocking and crosslinking step. This may be particularly advantageous for further reducing the overall process time. In certain embodiments, the three method steps of attaching the functional molecule, treatment with the oxidizing agent, and treatment with the di- or multivalent nucleophile may also be combined.

It is possible to finally stabilize the immobilized functional molecules, in particular if they are sensitive proteins, with a protective layer or coating for longer storage times. For example, the surfaces can be overcoated with an aqueous saccharide, polysaccharide, protein or polymer solution, which is then removed or dried, e.g. at atmospheric pressure, under negative pressure or in a vacuum. Suitable protective substances such as trehalose, pectin, gelatine or polyvinyl alcohol and corresponding processes are sufficiently known to the skilled person.

It is a particular distinction of the method according to the invention that it is suitable for surface functionalization of a wide variety of materials and for a wide variety of applications in an unexpectedly universal manner. The surface may comprise, for example, a plastic surface, a ceramic surface, a metal surface and/or a semiconductor surface. Films and molded bodies and semi-finished products of any shape, porous or fibrillar materials such as filter membranes, for example, can be functionalized with the method according to the present invention in the same way as micro- and nanoscale materials and particles, e.g. nanoparticles and microbeads. In preferred embodiments, the method comprises functionalizing a plastic surface, wherein the plastic is selected in particular from polystyrene, polyvinyl chloride and/or polycarbonate. In further preferred embodiments, plastics with particularly favorable optical properties, e.g., high transparency and low birefringence, as used for optical devices or diagnostic methods with optical detection, are functionalized using the method according to the invention. Advantageously, plastics such as COC (cycloolefin copolymers, brand name "Topas" from Topas Advanced Polymers GmbH, Germany; or Zeonex/Zeonor from Zeon Corporation, Japan), for example, can be functionalized using the method according to the invention without visibly altering their transparency and optical surface quality.

Accordingly, in a second aspect, the invention provides an article or a carrier having a surface which has been functionalized, at least in part, by a method according to the first aspect. In particular, the article according to the invention is characterized in that a polyphenol layer with at least one functional molecule attached to the polyphenol layer is arranged at least in a part on the surface, wherein a covalent bond is formed between the polyphenol layer and the functional molecule.

In a preferred embodiment, the functional molecule comprises a protein, in particular an antibody or an antigen. In a particularly preferred embodiment, at least two or more different functional molecules, for example two or more different proteins, in particular two or more different antibodies and/or two or more different antigens, are covalently attached to the polyphenol layer.

In a further embodiment, the polyphenol layer additionally comprises a crosslink between two or more polyphenol compounds, the crosslink being formed or capable of being formed in particular by a covalent bond of a di- or multivalent nucleophile, which is different from the functional molecule, to the polyphenol layer. In preferred embodiments, the crosslink or di- or multivalent nucleophile comprises a biological or synthetic polymer preferably selected from protein, protein fragment, peptide, polyethyleneimine, poly-L-lysine, polyvinyl alcohol, hydroxyethylcellulose, pectin and/or starch or a respective part thereof.

In a preferred embodiment, the article is a plastic article, in particular a disposable plastic article. In a particularly preferred embodiment, the article is a microplate or cell culture plate. In a further preferred embodiment, the article is a microfluidic device, for example a chip lab or so-called lab-on-a-chip device. In further embodiments, the article is a solid particle, particularly a microparticle or nanoparticle. In other embodiments, the article is a filter or membrane. In still other embodiments, the article is a medical device, for example, a prosthesis, an implant, an implantable data chip, an artificial vessel or organ, a catheter, a stent, a tube, a blood bag, a probe, a contact lens, or the like.

A third aspect of the invention provides a use of a method according to the first aspect and/or a use of an article according to the second aspect for technical, biotechnical and/or medical purposes. Technical purposes include, for example, separation and/or purification processes. Non-limiting examples for biotechnical purposes are, for example, analytical and/or diagnostic tests, in particular antibody-based or antigen-based detection methods (immunoassays) and here in particular those in the so-called ELISA format. Medical purposes include, in particular, applications in the field of prosthesis or implantation technology and in the field of hygiene.

Finally, in a fourth aspect the invention provides a kit for functionalizing a surface. The kit contains at least one polyphenol compound with which a polyphenol layer can be formed at least in a part of the surface, and subsequently at least one functional molecule can be attached to the polyphenol layer to functionalize the surface. In addition, the kit contains at least one oxidizing agent with which the polyphenol layer can be treated, at least in part, and converted or transformed into an oxidized form. Furthermore, the kit may be adapted for carrying out a method according to the first aspect and/or for producing an article according to the second aspect. It is provided, for example, that the kit includes one or more articles having the surface to be coated, such as microtiter plates.

In preferred embodiments, the oxidizing agent contained in the kit comprises hydrogen peroxide ($H_2O_2$), iodine ($I_2$) and/or iodide. Preferably, the kit contains the iodine and/or iodide at least partially as iodine-iodide or polyiodide-starch complex or in a form with which an iodine-iodide or polyiodide-starch complex can be prepared, e.g. as iodine-potassium iodide solution or iodine-sodium iodide solution. In this case, the kit may additionally contain starch, in particular water-soluble starch.

The kit may further include one or more buffers and/or buffer substances, e.g., in powder form, for preparing a buffered solution of the polyphenol compound, the oxidant, and/or for the functional molecule to bind to the polyphenol layer.

Preferred and advantageous embodiments of the article according to the second aspect of the invention, the use according to the third aspect of the invention and the kit according to the fourth aspect of the invention correspond, as far as applicable, to those of the method according to the first aspect of the invention. Features disclosed above and in the following for the method may therefore also relate to the article, the use and the kit, and vice versa.

BRIEF DESCRIPTION OF THE FIGURES

FIG. 1 shows the water contact angles in degrees (y-axis) of tannic acid layers on polystyrene as a function of the duration in minutes (x-axis) of an oxidative treatment with iodine or iodine starch of different composition. A: 2 milligrams per milliliter iodine; B: 0.4 milligrams per milliliter starch+0.02 milligrams per milliliter iodine; C: 4 milligrams per milliliter starch+0.2 milligrams per milliliter iodine; D: 40 milligrams per milliliter starch+2 milligrams per milliliter iodine; PS: untreated polystyrene (reference).

Figure 2:
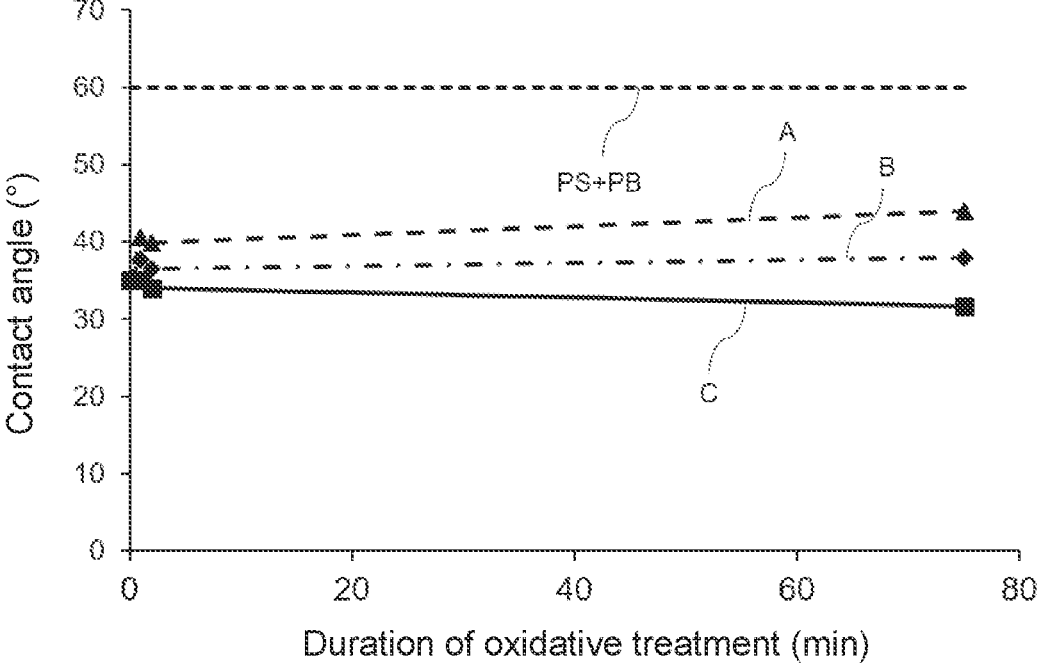
FIG. 2 shows a graph of the water contact angles in degrees of tannic acid layers on polystyrene as a function of the duration in minutes of an oxidative treatment with iodine or iodine starch followed by a 60-minute blocking or cross-linking step with 1% Perfect Block.

FIG. 2 shows the water contact angles in degrees (y-axis) of tannic acid layers on polystyrene as a function of the duration in minutes (x-axis) of an oxidative treatment with iodine or iodine starch followed by a 60-minute blocking or crosslinking step with 1% Perfect Block. A: 2 milligrams per milliliter iodine; B: 0.4 milligrams per milliliter starch+0.02 milligrams per milliliter iodine; C: 4 milligrams per milliliter starch+0.2 milligrams per milliliter iodine; PS+PB: untreated polystyrene with 1% Perfect Block (reference).

Figure 3:
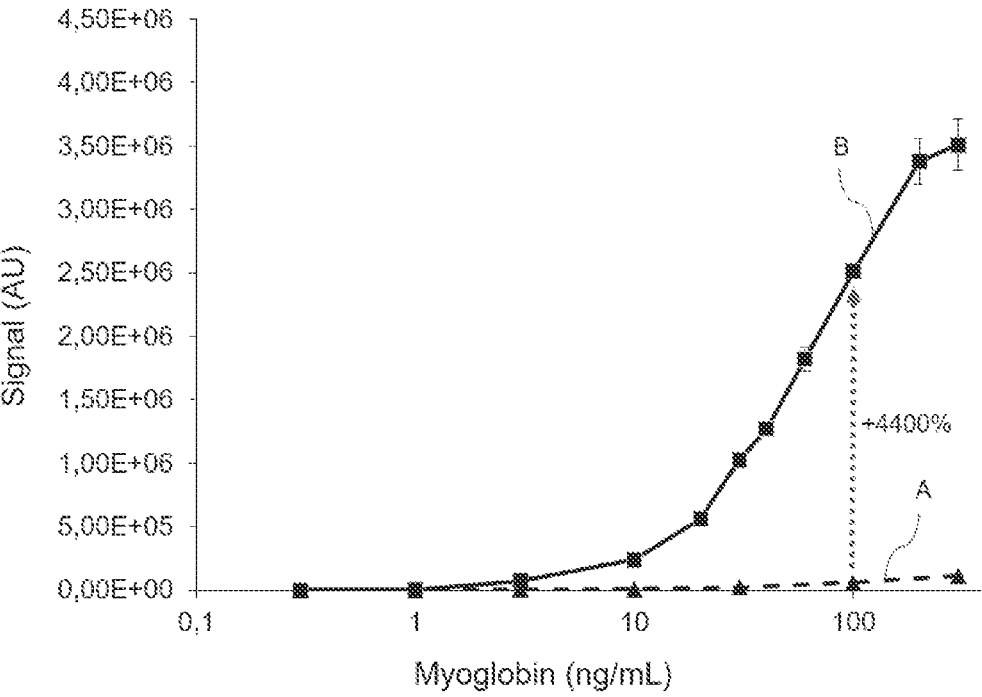
FIG. 3 shows a graph of dose-response curves of a sandwich immunoassay for the detection of myoglobin with a conventionally functionalized reference surface (A) and with a surface functionalized according to the method of the present invention (B).

FIG. 3 shows dose-response curves of a sandwich immunoassay for the detection of myoglobin with a conventionally functionalized reference surface (A) and with a surface functionalized according to the method of the present invention (B). Both surfaces were coated with the same amount of antibody and for the same time period of 15 min.

Figure 4:
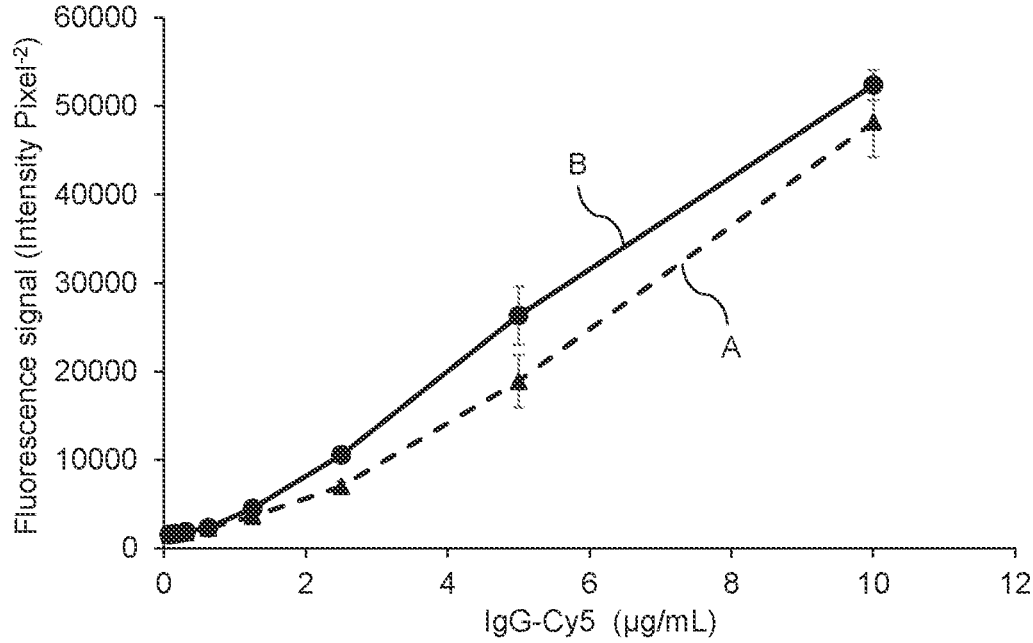
FIG. 4 shows a graph of the quantitative evaluation of the fluorescence signals of IgG-Cy5 on a conventionally functionalized surface (A) and a surface functionalized according to the invention (B) as a function of the IgG-Cy5 concentration used.

FIG. 4 shows the quantitative evaluation of the fluorescence signals of IgG-Cy5 (y-axis) on a conventionally functionalized surface (A) and a surface functionalized according to the invention (B) as a function of the IgG-Cy5 concentration used (x-axis).

Figure 5:
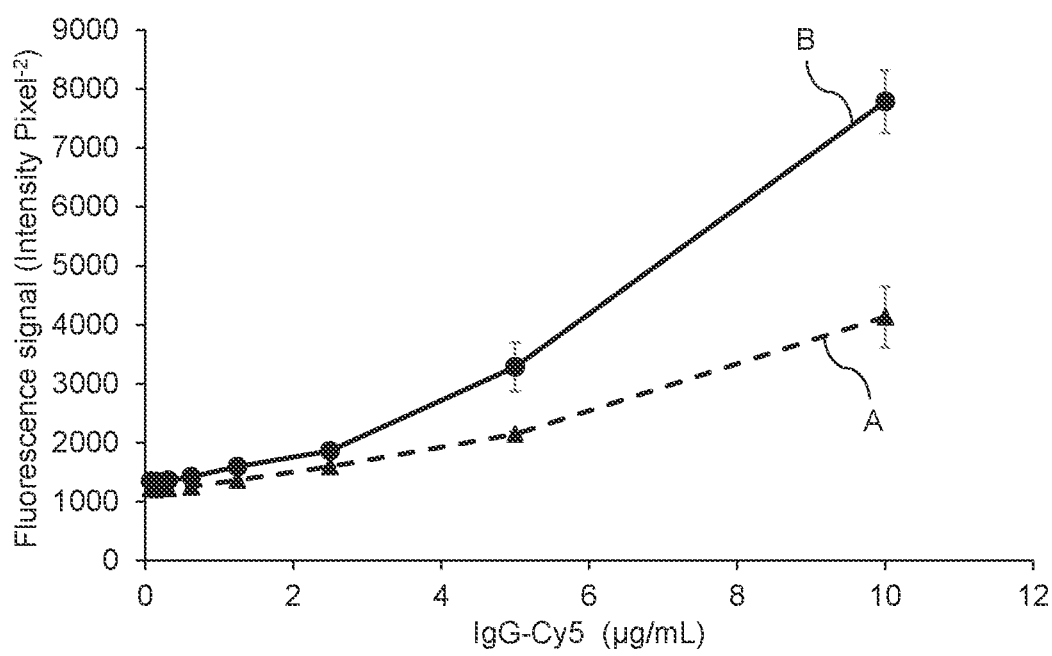
FIG. 5 shows a graph of the quantitative evaluation of the fluorescence signals of IgG-Cy5 on the conventionally functionalized surface (A) and the surface functionalized according to the invention (B) from FIG. 4 after blocking the surfaces with 1% Perfect Block.

FIG. 5 shows the quantitative evaluation of the fluorescence signals of IgG-Cy5 on the conventionally functionalized surface (A) and the surface functionalized according to the invention (B) from FIG. 4 after blocking the surfaces with 1; Perfect Block.

Figure 6:
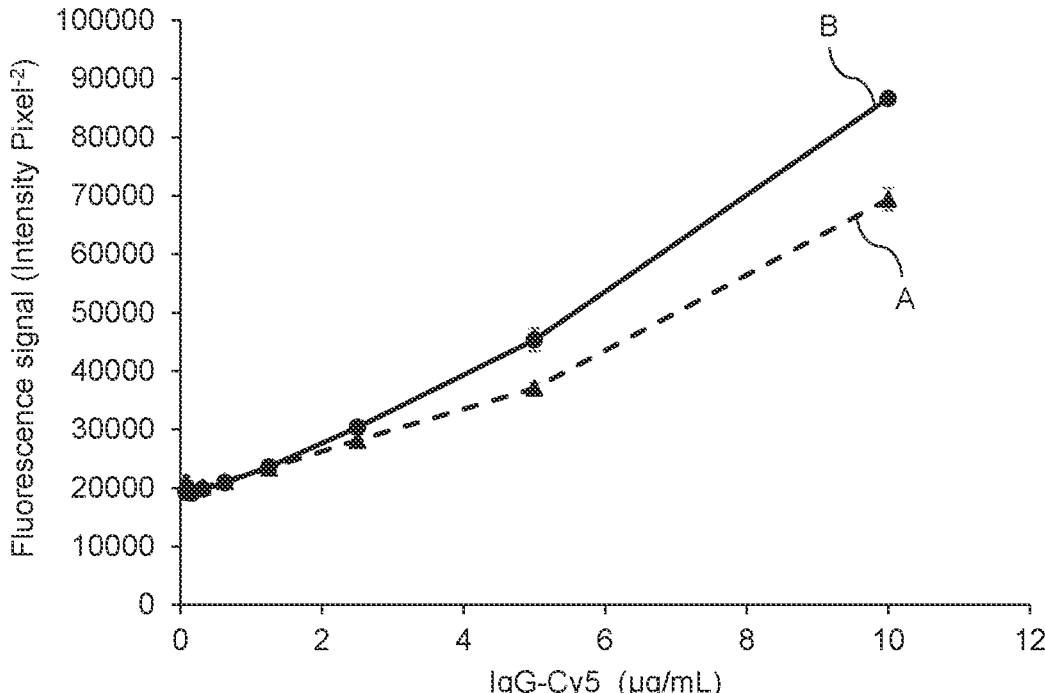
FIG. 6 shows a graph of the quantitative evaluation of the fluorescence signals of IgG-Cy5 on a conventionally functionalized surface (A) and another surface functionalized according to the invention (B) as a function of the IgG-Cy5 concentration used.

FIG. 6 shows the quantitative evaluation of the fluorescence signals of IgG-Cy5 (y-axis) on a conventionally functionalized surface (A) and another surface functionalized according to the invention (B) as a function of the IgG-Cy5 concentration used (x-axis).

Figure 7:
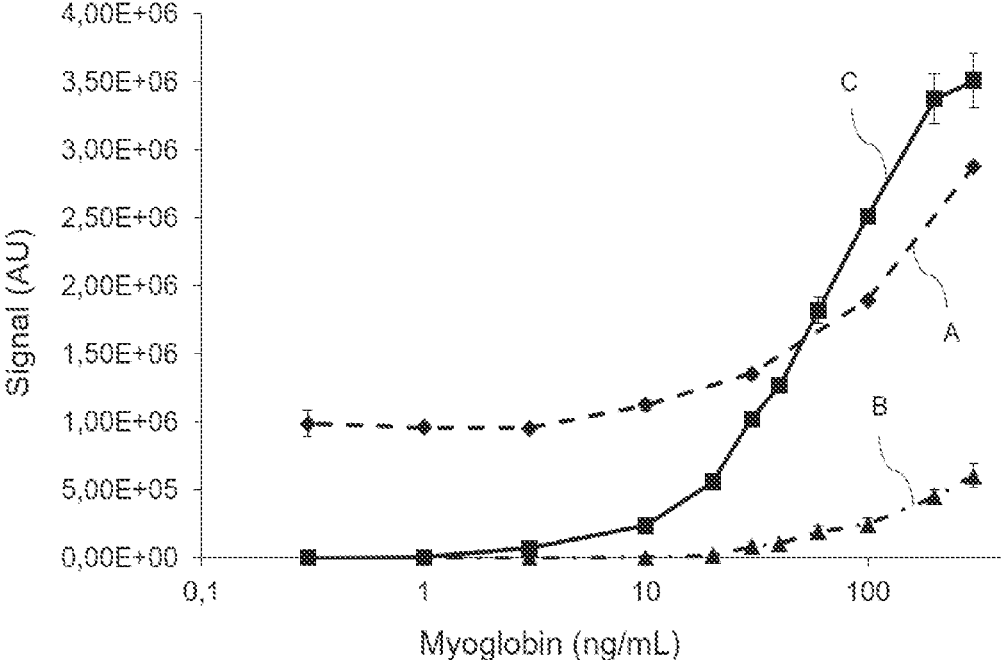
FIG. 7 shows a graph of dose-response curves of a sandwich immunoassay for the detection of myoglobin with conventionally functionalized polyphenol surfaces in each case without (A) and with blocking or crosslinking step (B) as reference and with a polyphenol surface functionalized according to the method of the present invention (C).

FIG. 7 shows dose-response curves of a sandwich immunoassay for the detection of myoglobin with conventionally functionalized polyphenol surfaces in each case without (A) and with blocking or crosslinking step (B) as reference and with a polyphenol surface functionalized according to the method of the present invention (C).

DETAILED DESCRIPTION OF EXAMPLES

In the following, the invention is explained in more detail by way of examples with reference to the figures and experimental data. The examples serve solely to illustrate the invention and not to limit the invention to specific details.

Example 1: Creation of a Polyphenol Layer on a Polystyrene Surface

Polyphenol layers were produced on a number of different surfaces. By way of example, the deposition of a polyphenol layer on a polystyrene surface as a representative hydrophobic or low-energy plastic surface is described here. Polystyrene is a widely used standard plastic for disposable plastic articles in daily laboratory use such as microtiter plates, cuvettes and cell culture vessels. In many applications, such as immunoassay manufacturing, it is necessary to functionalize the polystyrene surface with functional molecules such as antibodies or antigens.

First, a fresh coating solution containing tannic acid (Sigma-Aldrich, Germany), a preferred polyphenolic compound of the present invention, was prepared at a concentration of 1 millimole per liter or 1.7 grams per liter in phosphate-buffered physiological salt solution at pH 7.4 (Dulbecco's PBS buffer). The polystyrene surface was then covered with the coating solution and incubated for 60 minutes at room temperature (approximately between 20° C. and 25° C.) without shaking. At the end of the incubation, the excess coating solution was removed and the polystyrene surface was washed once with PBS buffer and dried.

The properties of the coated and uncoated polystyrene surfaces were then compared using a water contact angle measurement. The measurement was carried out using a DSA25 manual drop shape analyzer from Krüss GmbH, Germany according to the manufacturer's instructions. From the measurement of water contact angles, certain properties of the surface of a solid can be determined, such as the surface energy. The more the drop contracts on the surface, i.e. the larger the contact angle, the lower the surface energy of the solid.

FIG. 1 shows that the contact angle of the uncoated polystyrene surface (PS) is 90°. Treatment with the coating solution lowers the contact angle by 40° to about 50° (FIG. 1: time 0), i.e. the surface energy increases sharply and the surface becomes hydrophilic. This result shows that a suitable tannic acid layer was generated on the polystyrene surface within a short time.

Example 2: Comparison of Different Oxidation Treatments of the Polyphenol Layer The oxidation step, i.e. the treatment of the polyphenol layer with an oxidizing agent, is an essential step of the method according to the invention. In this example, the time-dependent influence of various oxidizing agents according to the invention on the polyphenol layer was investigated.

For this purpose, polystyrene surfaces coated with tannic acid were prepared according to Example 1 and then treated with an iodine solution at a concentration of 2 milligrams per milliliter (A) or with an iodine starch solution containing 0.4 milligrams per milliliter starch and 0.02 milligrams per milliliter iodine, (B) 4 milligrams per milliliter starch and 0.2 milligrams per milliliter iodine (C) or 40 milligrams per milliliter of starch and 2 milligrams per milliliter of iodine (D) each in PBS buffer pH 7.4 for a period of 75 minutes. A suitable iodine solution at a concentration of 2 milligrams per milliliter can be prepared, for example, from nine parts water and one part 2% Lugol's solution (2 grams sodium iodide and 1 gram iodine in 50 milliliters water; Sigma-Aldrich, Germany). An iodine starch solution suitable for dilution with 40 milligrams per milliliter of starch and 2 milligrams per milliliter of iodine can be prepared from nine parts of starch solution with 4 percent by weight soluble starch according to Zulkowsky (Sigma-Aldrich, Germany) in water and one part 2% Lugol's solution.

The results of this test are again shown in FIG. 1. The diagram shows the change in the contact angle (y-axis) as a measure of the surface energy or hydrophilicity of the treated surface over the treatment time in minutes (x-axis) as a function of the respective oxidizing agent. Treatment with iodine (A) alone leads to a decrease in surface energy due to the oxidation of high-energy phenolic groups to lower-energy quinone groups, which manifests itself in a corresponding increase in the contact angle above that of the untreated polyphenol layer. Treatment with the low concentration iodine starch solutions (B, C) results in only a slight overall decrease in surface energy. In contrast, at the highest concentration of iodine starch solution (D), the contact angle drops significantly below the contact angle of the untreated polyphenol surface due to an increase in surface energy, which is presumably caused by increased binding of hydrophilic starch molecules to the oxidized polyphenol layer.

In a further experiment, the additional influence of a 60-minute blocking and crosslinking step with a 1% (w/v) Perfect Block solution (MoBiTec GmbH, Germany) in PBS buffer on the surface energy was also investigated. FIG. 2 shows the results of this experiment, with the graph again showing the change in contact angle (y-axis) as a measure of the surface energy or hydrophilicity of the treated surface over the treatment time in minutes (x-axis) as a function of the respective oxidizing agent. Perfect Block lowers the contact angle of an untreated reference polystyrene surface (PS+PB) from 90° to about 60°. In contrast, the blocking and crosslinking step lowers the contact angle of the tannic acid layers to 35°. In this case, the additional treatment with elemental iodine (A) or diluted iodine starch (B) has little effect on the contact angle and surface energy. Only concentrated 4% iodine starch still slightly reduces the contact angle in this case (C).

Example 3: Comparison of the Active Antibody Amount of a Surface Functionalized According to the Present Invention and a Conventionally Functionalized Surface A main field of application of functionalized surfaces is the production of solid-phase reagents for analytical or diagnostic assays. One of the most common formats is the so-called enzyme-linked immunosorbent assay (ELISA) and in particular the sandwich ELISA. In this format, an antibody is bound to the surface of a solid phase, usually the polystyrene surface of a microtiter plate containing 96 separate wells. The sample containing the antigen to be detected is added to the wells and incubated. During this phase, the antibody bound to the plate binds the antigen present in the sample, which can then be detected or quantified in further steps. In the sandwich ELISA, the measurement signal is directly proportional to the amount of antibody present in functional or active form immobilized on the surface, i.e. the amount of antibody that has not been denatured by surface attachment. For this reason, the signal level or dynamic sensitivity of the sandwich ELISA provides direct information on how the amounts of active surface-bound antibody differ from one another in different functionalization procedures.

The aim of this experiment was to compare the active antibody amount of a microtiter plate functionalized in the usual industrial manner by direct adsorption of antibody to the polystyrene surface with the active antibody amount achieved in a microtiter plate with a polystyrene surface functionalized according to the present invention.

For reference functionalization (A), 0.3 micrograms per milliliter of anti-myoglobin monoclonal antibody (HyTest Ltd., Finland) was incubated in 50 microliters of PBS buffer in each well of the microtiter plate (Sarstedt AG, Germany) for 15 minutes with shaking. After removing the antibody solution, the surface of each well was incubated with 100 microliters of 1; (w/v) Perfect Block solution (MoBiTec GmbH, Germany) in PBS buffer for 60 minutes.

For functionalization (B) according to the present invention, a tannic acid layer was first generated in the wells of the microtiter plate analogous to Example 1. Then the antibody was bound to the tannic acid layer under the same conditions as described above under (A). After removing the antibody solution, the next step was the treatment with the oxidizing agent, wherein 100 microliters of an iodine starch solution (40 milligrams per milliliter of starch, 2 milligrams per milliliter of iodine) in PBS buffer pH 7.4 was incubated with the surface for 1 minute. The iodine starch solution was then removed and the surface was treated with Perfect Block as in (A).

For the following myoglobin assay, a concentration series of myoglobin (human myoglobin; Applichem GmbH, Germany) was first prepared in PBS buffer pH 7.4 at 0, 0.3, 1, 3, 10, 30, 100, and 300 nanograms per milliliter of myoglobin. Fifty microliters of each concentration was transferred to three different wells of the functionalized microtiter plates and incubated for 15 minutes without shaking. After removal of the myoglobin solution, each well was washed four times with 150 microliters each of PBST (PBS buffer pH 7.4+0.05% (v/v) Tween 20) and next incubated with 50 microliters each of a solution containing 0.23 micrograms per milliliter of polyclonal anti-myoglobin antibody-HRP conjugate (HyTest Ltd., Finland) in PBS buffer pH 7.4 for 15 minutes without shaking.

After washing four times with 150 microliters of PBST each, 50 microliters of luminescent substrate for ELISA (SuperSignal ELISA Pico Chemiluminescent Substrate, Thermo Fisher, Germany) was added to each well according to the manufacturer's protocol and luminescence development was immediately recorded continuously for 15 minutes in a luminescence reader (BMG Omega, Germany). The subsequent analysis was based on the luminescence signal after 6 minutes of each measured myoglobin concentration.

FIG. 3 shows the result of this experiment on the basis of the dose-response curves determined for the conventionally functionalized microplate (A) and the microplate modified according to the present invention (B). It is immediately apparent that the surface functionalization according to the invention leads to a significantly higher measurement signal at all tested concentrations, which is about 4400% above that of the conventionally functionalized surface in the linear measurement range. This estimate shows that, with the same amount of antibody and a contact time of 15 minutes, about 44 times more active antibody can be bound to the polystyrene surface using the method according to the present invention than with the conventional industrial method.

As a result, the method according to the invention can achieve previously unexpected savings in antibody use of at least 50% and up to 95% compared with conventional processes based on direct adsorption of the antibody in the preparation of immunoassay solid-phase reagents.

This distinctive effect of the combination of hydrophilic, biocompatible polyphenol coating and covalent attachment of the functional molecule to the polyphenol layer by means of treatment with an oxidizing agent, and the associated added value of the invention for the performance and economy of functionalized surfaces, could not have been expected from a skilled person's point of view.

Example 4: Comparison of Loading and Stability of Surfaces Functionalized According to the Present Invention and Conventionally Functionalized Surfaces WO 2014/116812 A2 describes the coating of technical surfaces with polyphenol layers to which, for example, a polymer or a protein can subsequently be adsorbed. The technically important adsorption of proteins is only mentioned using the example of lysozyme. Lysozyme is considered to be one of the proteins with the strongest tendency to adsorb to surfaces, i.e. it is not possible to conclude from the behavior of lysozyme the adsorption behavior of other proteins such as antibodies to such polyphenol layers. WO 2014/116812 A2 furthermore does not provide any information on the stability or reversibility of the binding of the protein to the polyphenol surface in the presence of other proteins and reagents or on how protein-repelling properties of the polyphenol surface can be achieved.

The aim of this experiment was therefore to directly compare the loading and stability of surfaces functionalized with a protein either using the process according to the present invention or in the conventional manner, i.e. without treating the polyphenol layer with an oxidizing agent.

As an example of a technically relevant protein, an antibody was used for functionalization, in this case immunoglobulin G from sheep labeled with the fluorescent dye Cy5 (hereafter "IgG-Cy5"; Sigma-Aldrich, Germany). IgG-Cy5 can be visualized and quantified directly on an engineered surface using fluorescence-based imaging techniques. In this way, the concentration of bound IgG-Cy5 on the respective surface can be determined.

To perform the experiment, 96-well polystyrene microtiter plates (Sarstedt AG & Co. KG, Germany) were filled per well with 150 microliters of a tannic acid solution at a concentration of 1 millimole per liter in PBS buffer and incubated at a temperature of 20° C. to 23° C. for one hour without shaking. The tannic acid solution was then removed and each well was washed with 300 microliters of deionized water and dried.

In the next step, two different variants of the method according to the present invention were carried out and each was compared with the state of the art.

In a first variant of the method according to the invention, the polyphenol layer was treated with an oxidizing agent prior to contacting with IgG-Cy5. For this purpose, one half of each of the microtiter plates coated with tannic acid was oxidized with an iodine starch solution. For this purpose, 1.0 gram of iodine and 2.0 grams of sodium iodide were first dissolved in 50 milliliters of deionized water and, separately, 20.0 grams of Zulkowsky starch were dissolved in 1.5 liters of deionized water. Subsequently, both solutions were combined to prepare the iodine starch solution. For the oxidation treatment, the wells of the microtiter plate were each filled with 150 microliters of the iodine starch solution and incubated at 20° C. to 25° C. for 5 minutes. The wells in the other half of the microtiter plate serving as a reference were incubated with PBS buffer during this time.

After removal of the iodine starch solution or of PBS buffer, the wells of the microtiter plate were filled with a dilution series of IgG-Cy5 at concentrations of 10 micrograms per milliliter, 5 micrograms per milliliter, 2.5 micrograms per milliliter, 1.25 micrograms per milliliter, 625 nanograms per milliliter, 313 nanograms per milliliter, 156 nanograms per milliliter, and 78 nanograms per milliliter in PBS buffer pH 7.4 and incubated for 16 hours at 23° C. in the dark. After removal of the antibody solution, the concentration of surface-bound IgG-Cy5 in the wells was quantified using a fluorescence imager and ImageQuant TL ArrayVersion 7.0 analysis software (GE Healthcare, United Kingdom).

Furthermore, to compare the stability of IgG-Cy5 binding to the surface functionalized according to the present invention and the conventionally functionalized surface, the wells were each incubated in a further step with 250 microliters of a 1% (w/v) Perfect Block solution (MoBiTec GmbH, Germany) in PBS buffer for 5 hours at 23° C. without shaking.

After removal of the Perfect Block solution, the concentration of surface-bound IgG-Cy5 in the wells was quantified again as described above.

The results of this experiment are shown in FIGS. 4 and 5. FIG. 4 shows the quantitative evaluation of the fluorescence signals on the surface of the wells as a measure of the amount of surface-bound IgG-Cy5 (y-axis) as a function of the concentration of IgG-Cy5 used during immobilization (x-axis) before treatment of the surface with Perfect Block solution. Shown for each concentration are the mean values and standard deviations from three different wells after conventional functionalization (A) and functionalization according to the present invention (B). On average, the surface loading with IgG-Cy5 on the surface functionalized according to the present invention (B) was thus about 13% higher than on the reference surface (A), which was not treated with the oxidizing agent according to the prior art.

FIG. 5, on the other hand, shows the corresponding quantitative evaluation for the amount of IgG-Cy5 that was still bound to the surface functionalized according to the present invention (B) and the reference surface (A) after treatment with Perfect Block solution. Accordingly, the surface concentration of IgG-Cy5 on the surface functionalized according to the invention (B) after blocking was about twice as high as on the functionalized reference surface (A), which was not treated with the oxidizing agent. Without being bound by theory, this significantly improved stability of the surface functionalized according to the present invention is attributed to the fact that a larger fraction of IgG-Cy5 was covalently bound to the polyphenol layer by the method according to the present invention and could not be displaced by the blocking reagent. In contrast, IgG-Cy5 was predominantly reversibly adsorbed on the conventionally functionalized surface, so that the antibodies could be released from the surface again during treatment with Perfect Block solution.

The significantly improved stability of the surface functionalized according to the present invention is particularly advantageous, for example, for the preparation of solid-phase reagents for diagnostics and, in particular, as a solid phase in ELISA tests, since such solid phases can also be used in concentrated biological solutions such as undiluted blood sera. In such concentrated biological solutions, conventionally functionalized solid phases containing predominantly reversibly adsorbed antibodies usually fail. One of the most important failure mechanisms is non-specific protein adsorption, which leads to partial displacement of the surface-bound antibodies and thus to incorrect measurement results, as demonstrated here using the reference surface.

In a second variant of the method according to the present invention, the polyphenol layer was treated with the iodine starch solution not before but during contacting with IgG-Cy5. For this purpose, half of the wells of one of the microtiter plates coated with tannic acid were filled in equal parts with iodine starch solution and a double-concentrated IgG-Cy5 solution, so that the final concentrations of IgG-Cy5 in the wells again corresponded to the above-mentioned concentrations of the first variant. The wells of the other half of the microtiter plate serving as a reference were filled in equal parts with the double-concentrated IgG-Cy5 solution and PBS buffer instead of the iodine starch solution. Incubation was then performed for 15 minutes on a horizontal shaker at 200-300 rpm in the dark. After removing the antibody solution and washing the wells with PBS buffer, the concentration of surface-bound IgG-Cy5 in the wells was quantified as described above.

The result of this experiment is shown in FIG. 6, again using the quantitative fluorescence intensity on the surface of the wells as a measure of the amount of surface-bound IgG-Cy5 (y-axis) as a function of the IgG-Cy5 concentration used during immobilization (x-axis). It was found that after the 15-minute incubation with the antibody solution, about 25% higher fluorescence signals were measured on the surface functionalized according to the present invention (B) than on the conventionally functionalized surface (A), which was not treated with the oxidizing agent. This means that in the variant of the functionalization method according to the present invention in which the polyphenol layer is treated with the oxidizing agent during the attachment of the functional molecule, about 25% more IgG-Cy5 molecules were bound to the surface per unit time than in the conventional process.

These comparative tests demonstrate the advantageous effect of the oxidative treatment of the polyphenol layer in the method according to the present invention with regard to the loading and stability of the functionalized surfaces and the correspondingly favorable properties of the articles produced in this way compared to the prior art.

Example 5: Investigation of the Influence of the Blocking and Cross-Linking Step In addition to a high active antibody quantity on the solid phase, it is important for analytical or diagnostic assays such as the sandwich ELISA that the measurement signal is close to zero in the absence of the substance to be detected (so-called "zero-dose response"). Only if both conditions are met in combination can a detection method fulfill the quality characteristics of high sensitivity or a low detection limit and a large dynamic measuring range. A problem is that the non-specific binding of proteins, for example serum proteins in a blood analysis, can produce interfering signals and lead to an incorrectly increased zero-dose response.

In this example, starting from a polystyrene microtiter plate with polyphenol coating, the influence of the oxidation step and/or the blocking or crosslinking step on the active antibody amount and the zero-dose response was investigated in more detail.

For this purpose, a polyphenol layer was generated in the wells of the microtiter plate with tannic acid as described in Example 1, to which monoclonal anti-myoglobin antibody was subsequently bound as described in Example 3. In a first variant, the surface functionalized in this way was used directly as a reference in the subsequent sandwich ELISA (A). In a second variant, the surface was additionally treated only with Perfect Block as a further reference (B). In the third variant according to the present invention (C), the polyphenol layer was oxidized by treatment with iodine starch solution and subsequently treated with Perfect Block. The respective treatment steps and the performance of the subsequent sandwich ELISA were carried out analogously to Example 3.

The results of this study are shown by the respective dose-response curves of the myoglobin sandwich immunoassay in FIG. 7. The antibody-functionalized polyphenol surface without additional treatment led to high non-specific signals (A). Although these could be significantly reduced by treatment with Perfect Block (B), this treatment resulted in a considerable loss of signal intensity and dynamic sensitivity of the measurement. This is an indication that the antibody, which was only adsorptively bound to the polyphenol layer, was displaced from the surface again to a significant extent by the blocking reagent. In contrast, the oxidative treatment of the polyphenol layer according to the present invention in conjunction with the subsequent blocking and cross-linking step resulted in high signals and low non-specific protein binding (C). About ten times more active antibody was present on the surface functionalized according to the present invention than on the non-oxidized polyphenol surface (A).

Although the invention has been explained on the basis of preferred embodiments relating to the preparation of solid-phase reagents for analytical or diagnostic methods and in particular immunoassays, suitable modifications, e.g. with regard to other materials or surfaces and/or other functional molecules, can easily be determined by the skilled person on the basis of the present description and the embodiments.

Accordingly, the invention is not limited to the examples by the description based thereon. Rather, the invention encompasses any new feature as well as any combination of features, which in particular includes any combination of features as described in embodiments that is included in the actual scope of the invention, even if this feature or combination itself is not explicitly stated in the embodiments or examples.

The invention claimed is:

1. A method for functionalizing a surface, comprising:
   forming a polyphenol layer in at least in part of a surface by applying at least one polyphenol compound, and
   subsequently functionalizing the surface by attaching at least one functional molecule to the polyphenol layer, and
   treating the polyphenol layer at least partially with an oxidizing agent before, during and/or after attaching the functional molecule,
   wherein the oxidizing agent is iodine, and
   wherein treating the polyphenol layer with the iodine comprises preparing an iodine-iodide-starch complex and subsequently contacting the polyphenol layer with the iodine-iodide-starch complex under conditions that result in the polyphenol compound being at least partially converted into an oxidized form.

2. The method according to claim 1, wherein treating the polyphenol layer with the oxidizing agent is carried out at least partially during the attachment of the functional molecule to the polyphenol layer.

3. The method according to claim 1, wherein a covalent bond is formed between the functional molecule and the polyphenol layer.

4. The method according to claim 1, wherein the polyphenol compound has at least one ortho-diphenol group which is converted to an ortho-quinone group by treatment with the oxidizing agent.

5. The method according to claim 1, wherein the polyphenol compound comprises a tannin and/or a catechin.

6. The method according to claim 1, wherein the polyphenol compound is selected from the group consisting of tannic acid, epigallocatechin, epicatechin gallate, epigallo-catechin-3-gallate, pyrogallol, and any combinations thereof.

7. The method according to claim 1, wherein the polyphenol layer is treated with the oxidizing agent for at least 10 seconds.

8. The method according to claim 1, wherein the polyphenol layer is treated with the oxidizing agent for not more than 75 minutes.

9. The method according to claim 1, wherein attaching the at least one functional molecule comprises contacting the polyphenol layer with a solution comprising at least 0.01 microgram per milliliter of the at least one functional molecule.

10. The method according to claim 9, wherein the solution contains at least one further functional molecule.

11. The method according to claim 9, wherein the polyphenol layer is contacted with the solution for at least 1 minute.

12. The method according to claim 9, wherein the polyphenol layer is contacted with the solution for not more than 120 minutes.

13. The method according to claim 1, wherein attaching the at least one functional molecule comprises contacting the polyphenol layer with a solution comprising not more than 10 milligrams per milliliter of the at least one functional molecule.

14. The method according to claim 1, wherein the functional molecule comprises a biomolecule.

15. The method according to claim 1, wherein the functional molecule comprises an antibody.

16. The method according to claim 1, further comprising treating the polyphenol layer at least partially with at least one di- or multivalent nucleophile after attaching the functional molecule, after and/or during treatment with the oxidizing agent.

17. The method according to claim 16, wherein the di- or multivalent nucleophile is selected from the group consisting of protein, protein fragment, peptide, polyethyleneimine, polylysine, polyvinyl alcohol, hydroxyethyl cellulose, pectin, starch, and any combinations thereof.

18. The method according to claim 1, wherein the surface is a surface for technical, biotechnical, and/or medical purposes.

19. The method according to claim 1, wherein the polyphenol compound comprises a gallotannin.

* * * * *